United States Patent
Van Dyke et al.

(10) Patent No.: US 6,516,947 B1
(45) Date of Patent: Feb. 11, 2003

(54) CONTAINERS HAVING A FRACTURE RECESS FOR OPENING THE CONTAINERS

(75) Inventors: Darrell W. Van Dyke, Libertyville, IL (US); Frederic J. Beutlich, Mundelein, IL (US)

(73) Assignee: Viridian Packaging Solutions, LLC, Gurnee, IL (US)

(*) Notice: Subject to any disclaimer, the term of this patent is extended or adjusted under 35 U.S.C. 154(b) by 0 days.

(21) Appl. No.: 09/637,439

(22) Filed: Aug. 11, 2000

(51) Int. Cl.$^7$ ................................................ B65D 83/10
(52) U.S. Cl. ............................ 206/361; 604/363; 604/1
(58) Field of Search ................................. 206/363, 210, 206/361; 604/1, 2, 3; 401/132

(56) References Cited

U.S. PATENT DOCUMENTS

| | | |
|---|---|---|
| 1,146,522 A | 7/1915 | Robert |
| 1,166,761 A | 1/1916 | Higgins |
| 1,221,227 A | 4/1917 | Schulz |
| 1,229,195 A | 6/1917 | Hamilton |
| 1,309,201 A | 7/1919 | Hollister |
| 1,573,648 A | 2/1926 | Sheely |
| 1,585,911 A | 5/1926 | Heublein |
| 2,058,251 A | 10/1936 | Nitardy et al. |
| 2,337,116 A | 12/1943 | Limbert et al. |
| 2,687,130 A | 8/1954 | Cohen |
| 2,786,238 A | 3/1957 | Shapero |
| 2,830,325 A | 4/1958 | Bray |
| 2,902,146 A | 9/1959 | Doherty |
| 2,954,144 A | 9/1960 | Elam et al. |
| 2,966,703 A | 1/1961 | Harman |
| 2,983,959 A | 5/1961 | Shapero et al. |
| 3,002,231 A | 10/1961 | Walker et al. |
| 3,163,160 A | 12/1964 | Cohen |
| 3,458,076 A | 7/1969 | Babcock |
| 3,487,146 A | 12/1969 | Tillotson |
| 3,513,830 A | 5/1970 | Kalayjian |

(List continued on next page.)

FOREIGN PATENT DOCUMENTS

| | | |
|---|---|---|
| EP | 0 357 261 | 3/1990 |
| GB | 2 332 493 | 6/1999 |
| JP | 2 82972 | 3/1990 |

Primary Examiner—Mickey Yu
Assistant Examiner—Jila M. Mohandesi
(74) Attorney, Agent, or Firm—Bell, Boyd & Lloyd LLC

(57) ABSTRACT

A closed plastic container has a plastic elongated sleeve which has a hollow interior. An exterior fracture recess extends from an exterior surface of the sleeve inward to form a reduced wall thickness for opening the container. The container is opened by squeezing or bending the container at the exterior fracture recess. The closed container may have an applicator material inside or outside of the container. A substance contained within the container is dispensed and applied when the container is opened at the fracture recess. An inner closed container having an exterior fracture recess can be contained within an outer closed container also having an exterior fracture recess.

30 Claims, 3 Drawing Sheets

U.S. PATENT DOCUMENTS

| | | | |
|---|---|---|---|
| 3,596,801 A | 8/1971 | Barnack |
| 3,614,245 A | 10/1971 | Schwartzman |
| 3,640,268 A | 2/1972 | Davis |
| 3,759,259 A | 9/1973 | Truhan |
| 3,774,609 A | 11/1973 | Schwartzman |
| 3,776,220 A | 12/1973 | Monaghan |
| 3,847,151 A | 11/1974 | D'Alessandro et al. |
| 3,906,071 A | 9/1975 | Cook et al. |
| 3,927,161 A | 12/1975 | Powell et al. |
| 3,958,571 A | 5/1976 | Benington |
| 3,978,187 A | 8/1976 | Fletcher et al. |
| 4,049,767 A | 9/1977 | Vaidya |
| 4,057,047 A | 11/1977 | Gossett |
| 4,138,132 A | 2/1979 | Doyle |
| 4,211,323 A | 7/1980 | Olsen |
| 4,218,155 A | 8/1980 | Weidner |
| 4,226,580 A | 10/1980 | Lupke et al. |
| 4,322,907 A | 4/1982 | Rowe |
| 4,432,749 A | 2/1984 | Snyder et al. |
| 4,434,126 A | 2/1984 | McGary, Jr. et al. |
| 4,458,811 A | 7/1984 | Wilkinson |
| 4,552,715 A | 11/1985 | Ando et al. |
| 4,586,604 A | 5/1986 | Alter |
| 4,657,134 A | 4/1987 | Woodworth et al. |
| 4,673,541 A | 6/1987 | Watanabe et al. |
| 4,695,241 A | 9/1987 | Ventimiglia |
| 4,749,655 A | 6/1988 | Monthony et al. |
| 4,800,116 A | 1/1989 | Ventimiglia et al. |
| 4,874,373 A | 10/1989 | Luther et al. |
| 4,878,827 A | 11/1989 | Muller |
| 4,927,012 A | 5/1990 | Rowe |
| 4,943,225 A | 7/1990 | Prater |
| 4,952,204 A | 8/1990 | Korteweg |
| 4,990,016 A * | 2/1991 | Seidler ............... 401/132 |
| 4,992,037 A | 2/1991 | Hwang |
| 5,035,348 A | 7/1991 | Seifert |
| 5,065,913 A | 11/1991 | Glasener |
| 5,089,205 A | 2/1992 | Huang et al. |
| 5,100,028 A | 3/1992 | Seifert |
| 5,129,566 A * | 7/1992 | Ogden et al. ............... 225/103 |
| 5,229,061 A | 7/1993 | Van Dyke et al. |
| 5,326,603 A | 7/1994 | Van Dyke et al. |
| 5,380,182 A | 1/1995 | Packard et al. |
| 5,511,654 A | 4/1996 | de la Rocha |
| 5,826,600 A | 10/1998 | Rowe et al. |
| 5,922,365 A | 7/1999 | Reichner |
| 6,039,487 A | 3/2000 | Kristiansen |
| 6,406,451 B1 | 6/2002 | Rowe |

* cited by examiner

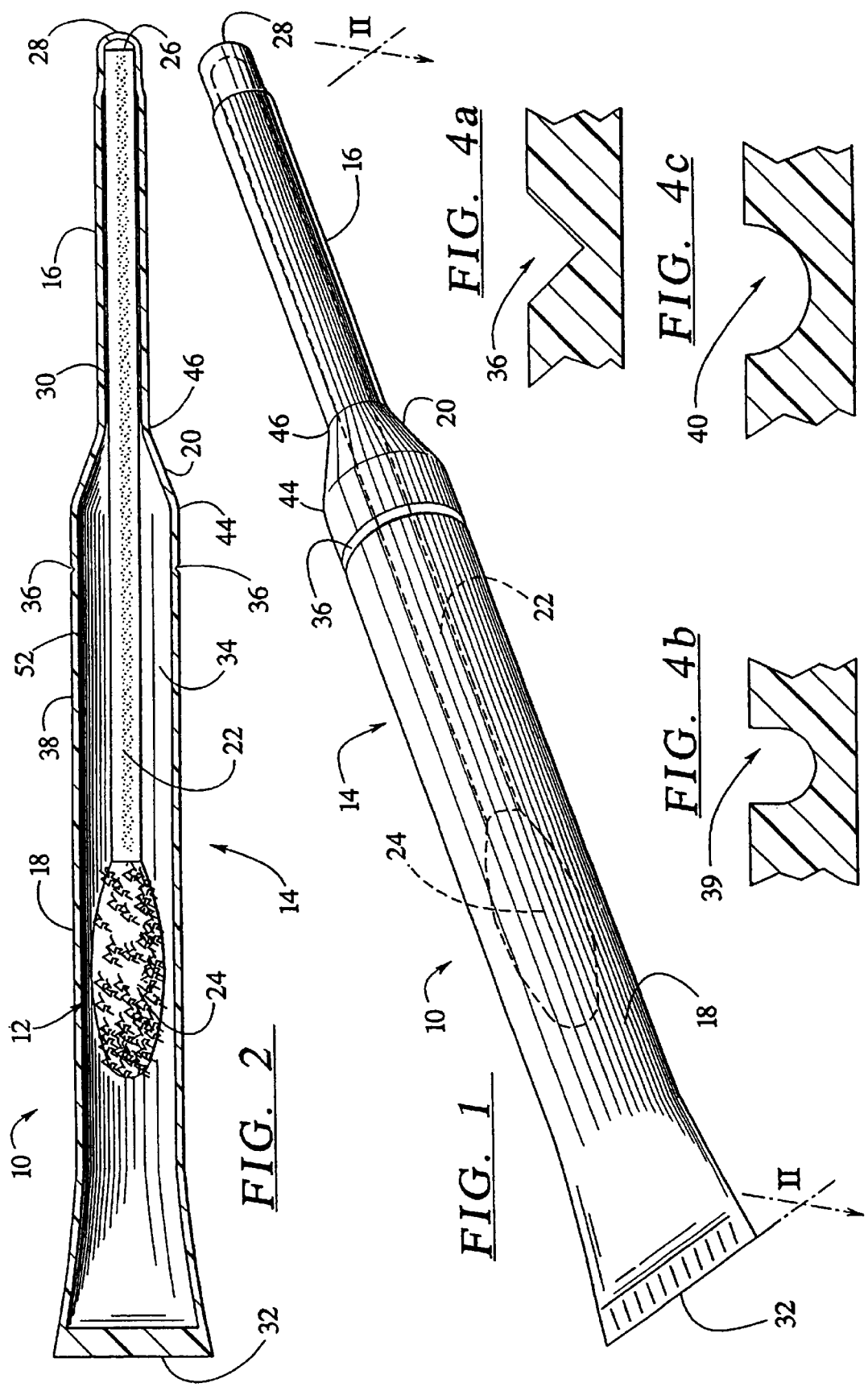

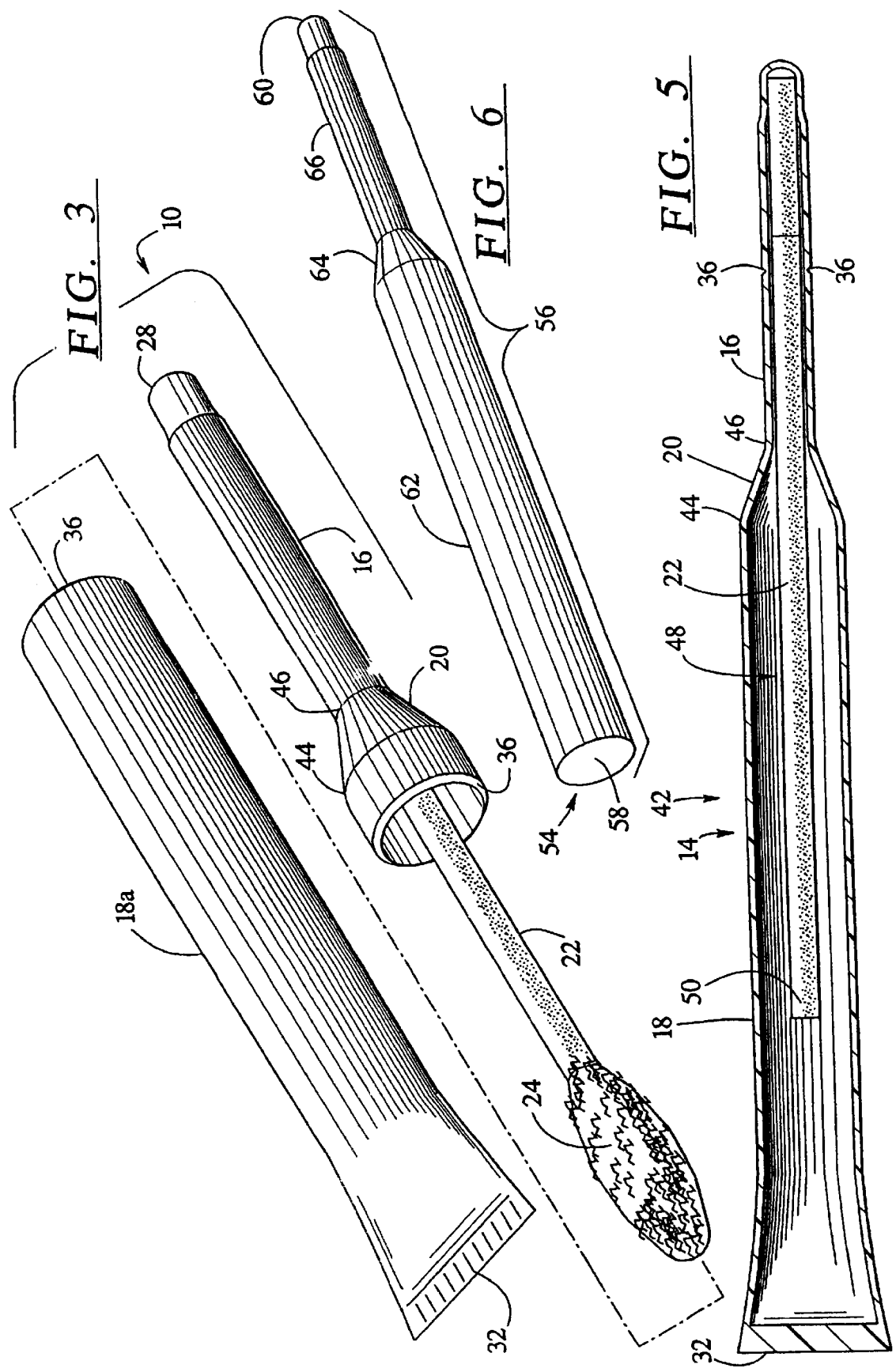

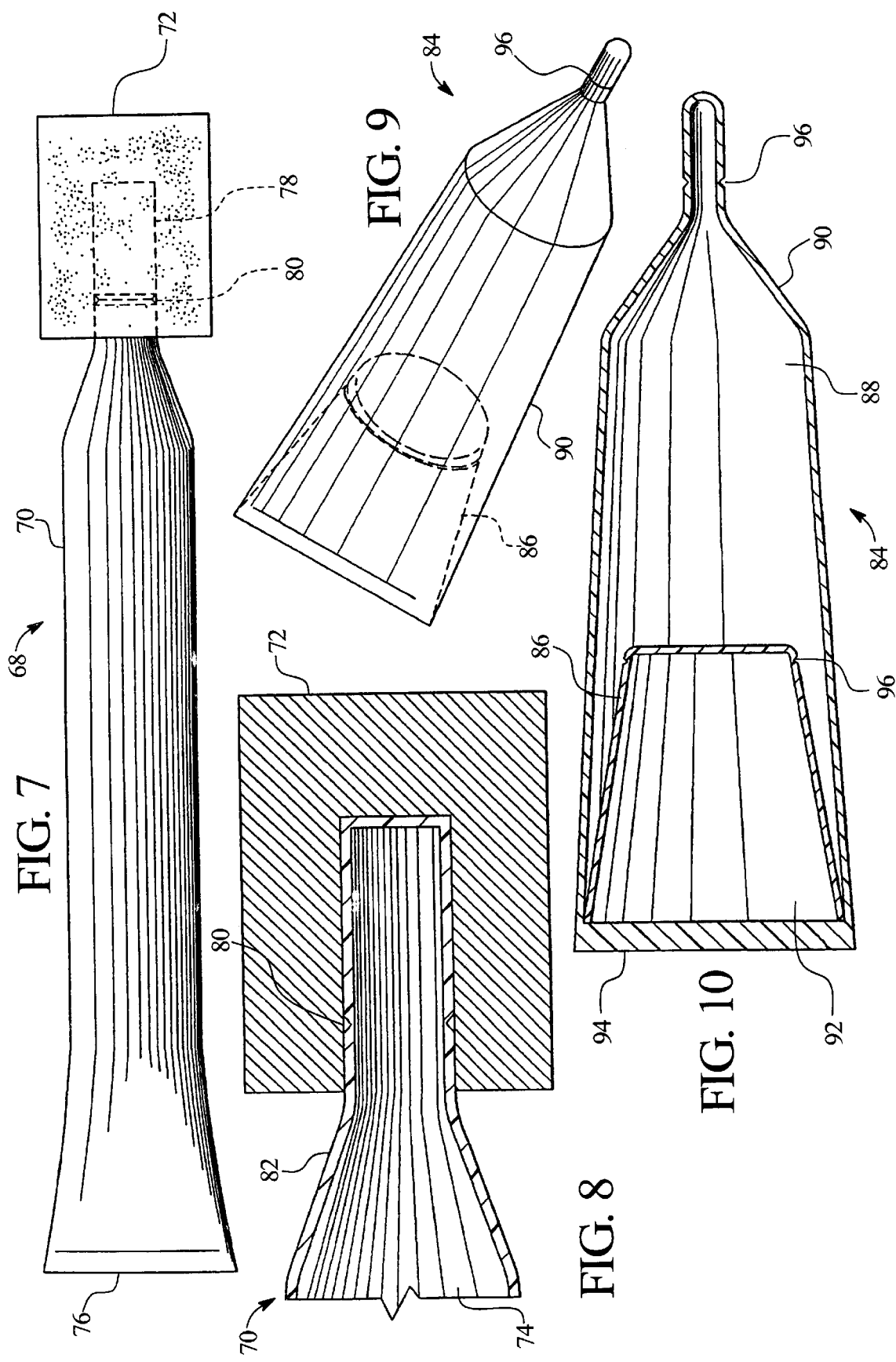

CONTAINERS HAVING A FRACTURE RECESS FOR OPENING THE CONTAINERS

FIELD OF THE INVENTION

The present invention generally relates to containers, and more specifically, the present invention relates to closed containers which have a fracture recess on an exterior surface for opening the containers. The closed containers may contain a substance, such as a medical fluid, which is dispensed and applied when the container is opened at the fracture recess. The present invention also relates to methods of making the containers and methods of using the containers.

BACKGROUND OF THE INVENTION

Swab applicators are one example of a product which has a container. Swab applicators typically include a swab having an applicator head connected to a handle. The swab is contained within a closed container package which can be opened to expose the swab for use. The swab may contain a medical fluid, for example, which can be applied to a patient.

One example of a swab applicator can be found in U.S. Pat. No. 4,952,204 entitled Dry Handle Swab Assembly Unit, which issued on Aug. 28, 1990. The '204 patent describes a swab contained within a sleeve which can readily be opened by use of manual force. The swab has a substance which can be applied by the swab. The swab has a straight hollow plastic stick with a bud of cotton attached on one end. The sleeve consists of a relatively small diameter cylindrical handle portion at one end, a substantially larger diameter receptacle portion at the opposite end, and a transition portion of compound configuration therebetween. A tip of the handle portion of the sleeve engages a tip of the swab stick. The intersection between the receptacle and transition portions forms a sharp angle on an interior of the sleeve. The sleeve is opened by squeezing the sleeve at the intersection between the receptacle and transition portions and breaking the sleeve at the interior sharp angle.

Examples of other containers include applicators or dispensers having sharp interior angles to open the containers, and include U.S. Pat. No. 4,927,012 entitled Packaging Assembly for Substances to be Post-Mixed, which issued on May 22, 1990, U.S. Pat. No. 5,229,061 entitled Mold and Method for Producing a Hollow Tube Component for a Dispensing Applicator, which issued on Jul. 20, 1993, and U.S. Pat. No. 5,326,603 entitled Hollow Tube Component for a Dispensing Applicator, which issued on Jul. 5, 1994.

Existing applicators and dispensers can be improved. For example, existing applicators and dispensers having sharp interior angles for opening the applicators and dispensers have a relatively complex structure. Molds having intricate shapes are required in order to manufacture such applicators and dispensers. Because of the intricate structure of the interior sharp angles which is used for opening the applicators and dispensers, there are limited locations on the applicators and dispensers where the sharp interior angle can be formed. Also, the exterior shape of the applicators and dispensers tend to be more intricate in the area of the interior sharp angle.

SUMMARY OF THE INVENTION

The present invention provides new containers which have a new structure for opening the containers. The new containers have a fracture recess on an exterior of the containers which allows for easy and reliable opening of the containers. The exterior fracture recess allows for flexibility where the fracture recess is located on the containers and thus, there is flexibility in locating the area where the containers are opened. A substance, such as a medical fluid or a powder, can be contained within the container and dispensed when the container is opened at the fracture recess. The new containers are easy to manufacture and can be manufactured by simple molds, such as a dip-mold to make a plastic container. The exterior fracture recess allows for labels to be applied on the outside of the containers such that the labels cover the fracture recess and provide advantageous appearance to the containers. The present invention also provides methods of making the containers and methods of using the containers.

Examples of the present invention include applicators and dispensers in general, and more specifically, swab applicators and pop ampule packages.

Various advantages of the present invention can become apparent upon reading this disclosure including the appended claims with reference to the accompanying drawings. The advantages may be desired, but not necessarily required to practice the present invention.

One plastic container according to the present invention has a plastic elongated sleeve which has a hollow interior. The elongated sleeve has a wall which has a wall thickness. A fracture recess extends from an exterior surface of the wall inward into the wall. The wall has a reduced wall thickness at the fracture recess. The fracture recess can have various shapes, such as a V-shape, U-shape, and wide U-shape.

One swab applicator according to the present invention has a closed package having a package handle connected to a swab head enclosure, a swab is contained within an interior of the closed package. The swab has a swab handle connected to the package handle and a swab head inside the swab head enclosure. A fracture recess extends inward from an exterior surface of the closed package.

Another swab applicator according to the present invention has a first tubular portion having a first cross-sectional area perpendicular to a longitudinal direction of the swab applicator, a second tubular portion having a second cross-sectional area perpendicular to the longitudinal direction which is smaller than the first cross-sectional area of the first tubular portion, and a connection portion between and connected to the first and second tubular portions. A closed interior is defined at least by the first tubular portion, the connection portion and the second tubular portion. A swab is contained within the closed interior and has a handle connected to the second tubular portion and a head within the first tubular portion. A fracture recess extends inward from an exterior surface of the at least one of the first tubular portion, the connection portion, and the second tubular portion.

An applicator package according to the present invention has a closed package having an interior sealed from an exterior of the closed package. The closed package has a fracture recess on an exterior surface of the closed package. An applicator material is positioned either in the interior of the closed package or on an exterior of the closed package.

Another swab applicator according to the present invention has a dip-molded closed package having a cylindrical package handle connected to a cylindrical swab head enclosure by a tapered section having a first end connected to the swab head enclosure and a second end connected to the package handle. A swab is contained within an interior of the closed package. The swab has a swab handle connected to the package handle and a swab head inside the swab head enclosure. A fracture recess extends inward from an exterior surface of the closed package.

One method of making a swab applicator according to the present invention includes the steps of dipping a dip mold in a reservoir of plastic material, removing the mold from the reservoir with a coating of plastic material on the dip mold forming a swab container, removing the swab container from the dip mold, forming a fracture recess on an exterior of the swab container, inserting a swab inside of the swab container, and sealing the swab container closed. A label can be adhered to the exterior of the swab container, for example, after the step of forming the fracture recess.

One method of opening a swab applicator according to the present invention pertains to swab applicator having a closed package having a package handle connected to a swab head enclosure. A swab is contained within an interior of the closed package. The swab has a swab handle connected to the package handle and a swab head inside the swab head enclosure. A fracture recess extends inward from an exterior surface of the closed package. The method includes the steps of squeezing or bending at the exterior recess, opening the closed package by fracturing the closed package at the exterior fracture recess, and exposing the swab head or the contents.

A dispenser package according to the present invention has an outer closed package which has a hollow interior. A portion of the outer closed package is openable. An inner closed package is contained inside of the outer closed package and has a hollow interior. A portion of the inner closed package is openable such that the interior of the inner closed package is in communication with the interior of the outer closed package. At least one of the openable portions of the outer and inner closed packages has an exterior fracture recess.

BRIEF DESCRIPTION OF THE DRAWINGS

FIG. 1 is a perspective view of a swab applicator according to the principles of the present invention.

FIG. 2 is a partial cross-sectional view of the swab applicator of FIG. 1 along the line II—II.

FIG. 3 is an exploded perspective view of the swab applicator of FIG. 1 after the swab applicator is opened.

FIG. 4a is an enlarged partial cross-sectional view of an exterior fracture recess of the swab applicator of FIG. 1.

FIG. 4b is an enlarged cross-sectional view of another exterior fracture recess.

FIG. 4c is an enlarged cross-sectional view of another exterior fracture recess.

FIG. 5 is a partial cross-sectional view of another swab applicator according to the principles of the present invention.

FIG. 6 is a perspective view of a dip mold according to the principles of the present invention.

FIG. 7 is a front elevational view of an applicator according to the principles of the present invention.

FIG. 8 is an enlarged, cross-sectional view of a portion of the applicator of FIG. 7.

FIG. 9 is a perspective view of a pop ampule package according to the principles of the present invention.

FIG. 10 is a cross-sectional view of the pop ampule package of FIG. 9.

DETAILED DESCRIPTION OF PRESENTLY PREFERRED EMBODIMENTS

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

The present invention generally pertains to plastic containers having an exterior fracture recess for opening the containers. However, specific examples of the present invention are shown and described, which include applicators/ dispensers having a swab or a pad, and a pop ampule package.

A new swab applicator 10 according to the principles of the present invention is shown by way of example in FIGS. 1 and 2. The swab applicator 10 has a swab 12 contained within a sealed package 14. The package 14 is sealed closed and provides a container to contain the swab 12. The package 14 has a package handle 16 at one end and a swab head enclosure 18 at an opposite end. A connection portion 20, such as a tapered section, connects the swab head enclosure 18 to the package handle 16.

Preferably, the package 14 has a generally elongated cylindrical shape. Accordingly the swab head enclosure 18 and the package handle 16 can have cylindrical shapes. The swab applicator 10 defines a longitudinal direction along the elongated direction of the package 14. The swab head enclosure 18 has a relatively larger diameter than a diameter of the package handle 16. Also, the cross-sectional area of the swab head enclosure 18 perpendicular to the longitudinal direction is greater than the cross-sectional area of the package handle 16 perpendicular to the longitudinal direction. The connection portion 20 is a tapered section which reduces in diameter and cross-sectional area perpendicular to the longitudinal direction to join the swab head enclosure 18 to the package handle 16.

The swab 12 is contained inside of the package 14, and has a swab handle 22 and a swab head 24 at one end of the swab handle 22. The swab head 24 may be made from a rayon or foam material or any other suitable material. The swab handle 22 has a distal end 26 which is engaged with an end 28 of the package handle 16 by an interference fit. A gap 30 may be provided between the package handle 16 and the portion of the swab handle 22 which is not engaged with end 28 of the package handle 16. The swab handle 22 has a length such that the swab head 24 is contained within the swab head enclosure 18 of the package 14.

The swab applicator 10, particularly the package 14, has a sealed end 32 opposite the end 28 of the package handle 16. The sealed end 32 may be sealed by various mechanisms, for example, heat sealing. Accordingly, the swab 12 is contained within an interior 34 of the sealed package 14.

The swab head 24 may contain various substances. For example, the swab head 24 may contain a medical fluid which can be applied to a patient during use of the swab applicator 10. The swab applicator 10 can also be used for purposes other than medical applications. For example, the swab applicator 10 could be used for application of cosmetics. Although the present invention is described as an applicator, a substance does not have to actually be applied by the swab 12 to practice the invention. For example, the swab applicator 10 can be used without a substance on the swab head 24 by using the swab 12 to collect a sample from another source.

The swab applicator 10 has a fracture recess 36 on an exterior surface 38 of the package 14. The fracture recess 36 extends from the exterior surface 38 towards the interior 34 of the package 14. The fracture recess 36 is a reduced material thickness of the wall of the package 14 which creates a structurally weak area in the package 14. The fracture recess 36 is located on the swab head enclosure 18. Preferably, the fracture recess 36 circumscribes the swab head enclosure 18 of the package 14. Although, the fracture recess 36 may extend around only a portion of the exterior surface 38 of the package 14.

The swab applicator 10 is used by breaking the package 14 open at the exterior fracture recess 36. The package 14 is fractured at the fracture recess 36 by creating stress in the package material at the location of the fracture recess 36. For example, the package 14 can be squeezed or bent at the fracture recess 36 which creates stress at the fracture recess 36. At least a portion of the wall of the package 14 will fracture at the fracture recess 36.

Referring to FIG. 3, a portion 18a of the swab head enclosure 18 is severed from the remainder of the package 14. The severed portion 18a of the swab head enclosure 18 is removed to expose the swab head 24 of the swab 12. If the severed portion 18a of the swab head enclosure 18 is not completely severed from the remainder of the package 14, the connection between the severed portion 38 and the remainder of the package 14 may form a hinge such that the severed portion 38 can be bent back on the hinge to expose the swab head 24.

The fracture recess 36 has a V-shape as shown in the enlarged cross-sectional view of FIG. 4a. However, the fracture recess 36 may have many different shapes. For example, FIG. 4b shows a fracture recess 39 having a U-shape, and FIG. 4c shows a fracture recess 40 having a wide U-shape.

The fracture recess 36 can be placed at any desired location along the elongated package 14. For example, FIG. 5 shows a partial cross-sectional view of another swab applicator 42. The swab applicator 42 has a package 14 in which the fracture recess 36 is located in the package handle 16. Other locations for the fracture recess 36 include, for example, the connection portion 20, a junction 44 between the swab head enclosure 18 and the connection portion 20, and a junction 46 between the connection portion 20 and the package handle 16. The location of the fracture recess 36 in the swab applicator 10 of FIG. 2 is located in the swab head enclosure 18 at a distance away from the junction 44 between the swab head enclosure 18 and the connection portion 20. Referring back to FIG. 5, another swab 48 usable with the swab applicator 42 is shown. Similar to the swab 12 shown in FIG. 2, the swab 48 has a swab handle 22. However, the swab head 50 of the swab 48 is not an enlarged head. For example, the swab head 50 may just be a portion of a plastic swab handle 22. The swab head 50 may be absorbent or non-absorbent as desired. The swab 48 could be used to spread a substance supplied from another source, for example. The swab 48 can be advantageous when the fracture recess 36 is located in the package handle 16 because when the package 14 is opened minimal or no wiping of the swab head 50 will occur by removing the severed portion of the package 14.

Referring to FIG. 2, the interior diameter of the swab head enclosure 18 along the longitudinal length of the swab head enclosure 18 is substantially constant. Although, there is a slight decrease in the inside diameter of the swab head enclosure 18 from the sealed end 32 toward the package handle 16. The package handle 16 may also have a slight taper of the inside diameter reducing in diameter toward the end 28. The slight tapering of the inside diameters of the package 14 facilitates removal of the package 14 from a dip mold. As shown in FIG. 2, the inside diameter of the swab head enclosure 18 and as shown in FIG. 5 the inside diameter of the package handle 16 are substantially constant above and below the fracture recesses 36. In other words, the interior surface 52 in the area of the fracture recess 36 has a smooth contour.

A dip mold 54 for use in making the swab applicator 10 is shown in FIG. 6. The dip mold 54 has a smooth exterior surface 56 from an end 58 to an opposite end 60. The end 58 of the dip mold 54 creates an open end of the package 14 which is then closed and sealed to form the sealed end 32 of the package 14. Of course, the end 60 of the dip mold 54 forms the end 28 of the package handle 16. The dip mold 54 has a swab head enclosure molding portion 62 connected to a connection portion molding portion 64 which is connected to a package handle molding portion 66. Of course the molding portions 62, 64, 66 respectively mold the swab head enclosure 18, the connection portion 20, and the package handle 16 of the package 14.

Referring to FIGS. 1, 2, and 6, a method of making the swab applicator 10 will now be described. The package 14 is made by a dip molding process. The dip mold 54 which has an exterior shape the same shape as the interior of the package 14 is heated and dipped into a reservoir of plastic material. The plastic material fluidly forms around the dip mold 54 and coats the dip mold 54 with a coating of the plastic material. The dip mold having the coating of plastic material is removed from the reservoir and the plastic material is cooled which forms a container. The package 14 is removed from the dip mold 54, and at this stage has an opened end which will later be sealed closed to form the sealed end 32. The fracture recess 36 is provided on the exterior of the package 14. For example, the fracture recess 36 may be carved as a score line into the package 14 by a knife. The swab 12 is inserted into the package 14 and the end 26 of the swab handle 22 is engaged with the end 28 of the package handle 16. The open end of the package 14 is heat sealed closed to form a sealed end 32 and enclose the swab 12 within the package 14.

The fracture recess 36 can be formed in various ways and at various stages during the manufacture of the swab applicator 10. For example, the fracture recess 36 can be provided before or after the package 14 is removed from the dip mold 54 or after the swab 12 is sealed closed within the package 14.

FIGS. 7 and 8 show another applicator/dispenser package according to the present invention. The applicator 68 has a closed container 70 and an applicator pad 72. The container 70 is an elongated plastic dip-molded cylindrical sleeve and has a hollow interior 74. The container 70 has a sealed end 76 opposite a dispensing end 78 which has a reduced diameter. An exterior fracture recess 80 is provided at the dispensing end 78 and circumscribes the container 70. The exterior fracture recess extends from an outer surface 82 of the container 70 inward and forms a reduced material thickness in the wall of the container 70.

The applicator pad 78 is provided on the outside of the container 70 at the dispensing end 78, and preferably circumscribes the dispensing end 78. The applicator pad 78 is adhered to the container 70 by an adhesive, for example, and covers the fracture recess 80. A fluid or other material to be dispensed is contained in the hollow interior 74 of the closed applicator package 86.

The applicator package 68 is used by opening the container 70 at the fracture recess 80. The container 70 is squeezed or bent at the fracture recess 80 and the wall of the container 70 breaks open at the fracture recess 80. The substance contained in the interior 74 of the container 70 can flow into the applicator pad 72 for application as desired. Squeezing the flexible container 70 may assist the substance to flow into the applicator pad 72.

When the container 70 is opened, the fracture recess 80 may remain partially intact (fracture only partially around the container 70) or may be fully severed around the container. The applicator pad 72 is adhered to the container 70 on the left and right sides of the fracture recess 80 as viewed in FIGS. 7 and 8. Accordingly, the applicator pad 72 holds the severed portions of the container 70 together.

A pop ampule package 84 is shown in FIGS. 9 and 10. The pop ampule package 84 has an inner container 86 contained within a hollow interior 88 of an outer container 90. The inner and outer containers 86, 90 are both sealed closed, and a hollow interior 92 of the inner container 86 is sealed from the interior 88 of the outer container 90. The inner and outer containers 86, 90 can contain substances which are maintained separate from each other until it is desired to mix the substances together. The inner and outer containers 86, 90 are elongated, plastic dip-molded cylindrical sleeves which are sealed together at an end 94 of the pop ampule package 84.

Both of the inner and outer containers 86, 90 are openable. One or both of the inner and outer containers 86, 90 has an exterior fracture recess 96 for opening the container. If only one of the inner and outer containers 86, 90 has the exterior fracture 96, the other container can be opened by any other suitable manner. For example, the outer container 90 can be opened by cutting the reduced diameter end.

The pop ampule package 84 is used by opening the inner container 86 by squeezing or bending the inner container 86 at the fracture recess 96. The interiors 92, 88 of the inner and outer containers 86, 90 are in communication with each other and the substances within the inner and outer containers 86, 90 can be mixed together. Next, the outer container 90 is opened by squeezing or bending at its fracture recess 96. The mixed substances can be dispensed and applied from the pop ampule package 84.

While the presently preferred embodiments have been illustrated and described, numerous changes and modifications can be made without significantly departing from the spirit and scope of this invention. Therefore, the inventors intend that such changes and modifications are covered by the appended claims.

The invention is claimed as:

1. A plastic container comprising:
   a plastic elongated sleeve having a hollow interior and an inside diameter which is reduced in dimension at a first end portion of the sleeve relative to an opposite second end portion of the sleeve, the elongated sleeve having a wall having a wall thickness;
   an inside diameter reduction transition portion between the first and second end portions;
   a swab head in the hollow interior at the second end portion of the sleeve; and
   a fracture recess extending from an exterior surface of the wall inward into the wall and positioned at a location on the second end portion of the sleeve spaced away from a junction between the second end portion and the transition portion, the wall having a reduced thickness at the fracture recess.

2. The plastic container of claim 1, wherein the elongated sleeve is sealed closed.

3. The plastic container of claim 1, wherein the elongated sleeve is a dip-molded sleeve having opposite closed ends.

4. The plastic container of claim 1, wherein the fracture recess circumscribes the elongated sleeve.

5. The plastic container of claim 1, wherein the elongated sleeve has a substantially cylindrical shape, and the inside diameter of the elongated sleeve is substantially constant from a location above the fracture recess to a location below the fracture recess.

6. The plastic container of claim 1, wherein the fracture recess has a V-shape.

7. The plastic container of claim 1, wherein the fracture recess has a U-shape.

8. The plastic container of claim 1, wherein the fracture recess has a wide U-shape.

9. The plastic container of claim 1, wherein an interior surface of the wall of the elongated sleeve opposite the fracture recess has a smooth contour.

10. The plastic container of claim 1, wherein the fracture recess is a score line cut into the wall.

11. The plastic container of claim 1, wherein the swab head is an applicator material connected to a swab handle.

12. The plastic container of claim 1, wherein the elongated sleeve is uniformly tapered from the one sleeve end portion to the opposite sleeve end portion.

13. A swab applicator comprising:
   a closed package having a package handle connected to a swab head enclosure, the swab head enclosure and the package handle have cylindrical shapes and the swab head enclosure having a larger diameter than the package handle, and further comprising a tapered section having a first end connected to the swab head enclosure and a second end connected to the package handle;
   a swab contained within an interior of the closed package, the swab having a swab handle connected to the package handle and a swab head inside the swab head enclosure; and
   a fracture recess extending from an exterior surface of the closed package into a wall of the closed package and being located at a position on the swab head enclosure spaced away from a junction between the swab head enclosure and the first end of the tapered section.

14. The swab applicator of claim 13, wherein the fracture recess circumscribes the closed package.

15. The swab applicator of claim 13, wherein the swab head enclosure has a cylindrical shape, and an interior diameter of the swab head enclosure is substantially constant from a location above the fracture recess to a location below the fracture recess.

16. The swab applicator of claim 13, wherein the fracture recess has a V-shape.

17. The swab applicator of claim 13, wherein the fracture recess has a U-shape.

18. The swab applicator of claim 13, wherein the fracture recess has a wide U-shape.

19. The swab applicator of claim 13, wherein an interior surface of the closed package opposite the fracture recess has a smooth contour.

20. The swab applicator of claim 13, wherein the fracture recess is a score line cut into the closed package.

21. The swab applicator of claim 13, wherein the closed package is a one-piece dip-molded package.

22. A swab applicator comprising:
   a firs tubular portion;
   a second tubular portion having a smaller diameter than the first tubular portion;
   a connection portion between and connected to the first and second tubular portions the first tubular portion, the connection portion, and the second tubular portion being a one-piece dip-molded container;

closed interior defined at least by the first tubular portion, the connection portion, and the second tubular portion;

a swab contained within the closed interior, the swab having a handle connected to the second tubular portion and a head within the first tubular portion; and a fracture recess extending from an exterior surface of the one-piece dip-molded container into a wall of the first tubular portion and being located at a portion of the container having a substantially constant inside diameter.

23. An applicator package comprising:

a closed package having an interior sealed from an exterior of the closed package, the closed package having a first inside diameter at one end portion which is greater than a second inside diameter at an opposite end portion, the closed package having an inside diameter transition portion between the end portions and a fracture recess on an exterior surface of the end portion having the greater diameter at a position spaced away from a junction between the end portion having the greater diameter and the transition portion; and an applicator material positioned in the interior of the closed package at the end portion having the greater diameter.

24. The applicator package of claim 23, wherein the applicator material comprises a swab contained within the interior of the closed package.

25. The applicator package of claim 23, wherein the closed package has an elongated tubular shape and the fracture recess circumscribes at least a portion of the exterior surface of the closed package such that the interior is exposed for use when the closed package is opened along the fracture recess.

26. The applicator package of claim 23, wherein the closed package is a dip-molded sleeve having opposite closed ends.

27. A swab applicator comprising:

a dip-molded closed package having a cylindrical package handle connected to a cylindrical swab head enclosure by a tapered section having a first end connected to the swab head enclosure and a second end connected to the package handle;

a swab contained within an interior of the closed package, the swab having a swab handle connected to the package handle and a swab head inside the swab head enclosure; and a fracture recess extending from a, exterior surface of the swab head enclosure into a wall of the swab head enclosure and spaced away from the connection of the swab head enclosure to the tapered section.

28. The swab applicator of claim 27, wherein the fracture recess is an exterior score line that circumscribes the swab head enclosure.

29. A method of opening a swab applicator having a closed package having a package handle connected to a swab head enclosure by a tapered section, a swab contained within an interior of the closed package, the swab having a swab handle connected to the package handle and a swab head inside the swab head enclosure, and a fracture recess extending into an exterior surface of the swab head enclosure, comprising the steps of:

bending the swab head enclosure at the exterior fracture recess;

opening the closed package by fracturing the swab head enclosure at the exterior fracture recess away from a junction between the swab head enclosure and the tapered section; and exposing the swab head.

30. A method of opening a swab applicator having a closed package having a package handle connected to a swab head enclosure by a tapered section, a swab contained within an interior of the closed packages the swab having a swab handle connected to the package handle and a swab head inside the swab head enclosure, and a fracture recess extending into an exterior surface of the swab head enclosure, comprising the steps of:

squeezing the swab head enclosure at the exterior fracture recess;

opening the closed package by fracturing the swab head enclosure at the exterior fracture recess away from a junction between the swab head enclosure and the tapered section; and exposing the swab head.

* * * * *